United States Patent [19]

Steer et al.

[11] Patent Number: 4,983,172

[45] Date of Patent: Jan. 8, 1991

[54] CLIP FOR DRAINABLE OSTOMY POUCH

[75] Inventors: Peter L. Steer; John V. Edwards, both of East Grinstead, England

[73] Assignee: Kingsdown Medical Consultants, Great Britain

[21] Appl. No.: 438,959

[22] Filed: Nov. 16, 1989

Related U.S. Application Data

[63] Continuation of Ser. No. 898,871, Aug. 20, 1986, abandoned, which is a continuation of Ser. No. 268,037, May 28, 1981, abandoned.

[30] Foreign Application Priority Data

May 29, 1980 [GB] United Kingdom ................ 8017515
Oct. 20, 1980 [GB] United Kingdom ................ 8033777

[51] Int. Cl.$^5$ .................... A61M 31/00; A61F 5/445; B65D 77/10
[52] U.S. Cl. .................. 604/332; 604/277; 604/335; 604/321; 24/30.5 R; 24/30.5 P
[58] Field of Search ............ 150/5, 6; 24/225 R, 24/17 A, 17 R, 16 R, 30.5 R, 30.5 W, 30.5 P, 16 PB, 334; 604/332-345

[56] References Cited

U.S. PATENT DOCUMENTS

| | | | |
|---|---|---|---|
| 2,520,831 | 8/1950 | Chincholl | 128/283 |
| 2,638,898 | 5/1953 | Perry | 604/340 |
| 2,818,069 | 12/1957 | Fenton | 128/283 |
| 2,902,036 | 9/1959 | Perry | 128/283 |
| 3,039,464 | 6/1962 | Galindo | 128/283 |
| 3,385,298 | 5/1968 | Fenton | 128/283 |
| 3,507,282 | 4/1970 | Burding | 128/283 |
| 3,523,534 | 8/1970 | Nolan | 128/283 |
| 3,570,490 | 3/1971 | Berger | 604/332 |
| 3,571,861 | 3/1971 | Olson | 24/30.5 P |
| 3,618,606 | 11/1971 | Brown et al. | 128/283 |
| 3,690,320 | 10/1972 | Riely | 128/283 |
| 3,755,859 | 9/1973 | Solari | 24/16 PB |
| 3,780,739 | 12/1973 | Frank | 128/283 |
| 3,825,005 | 7/1974 | Fenton | 128/283 |
| 3,865,109 | 2/1975 | Elmore | 128/283 |
| 4,022,863 | 5/1977 | Karass et al. | 24/16 R |
| 4,183,120 | 1/1980 | Thorne | 24/16 R |
| 4,296,529 | 10/1981 | Brown | 24/30.5 P |
| 4,317,262 | 3/1982 | Wells | 24/16 PB |

FOREIGN PATENT DOCUMENTS

| | | |
|---|---|---|
| 2547875 | 4/1977 | Fed. Rep. of Germany ...... 604/332 |
| 141035 | 1/1921 | United Kingdom . |
| 826308 | 12/1959 | United Kingdom . |
| 1224535 | 3/1971 | United Kingdom . |
| 1245677 | 9/1971 | United Kingdom . |

Primary Examiner—Randall L. Green
Assistant Examiner—Robert Clarke
Attorney, Agent, or Firm—Stephen B. Davis

[57] ABSTRACT

An integral hinged clip having two limbs. One limb is held by two opposed resilient catch portions of the other limb within a channel defined by said other limb. The catch portions effecting said holding in their normal undeformed positions. The clip is useful as a closure for a drainable ostomy pouch.

6 Claims, 2 Drawing Sheets

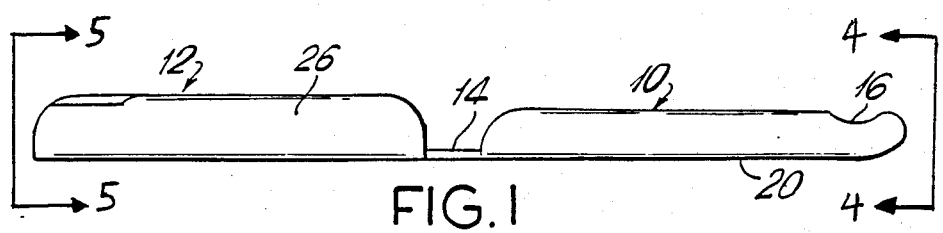
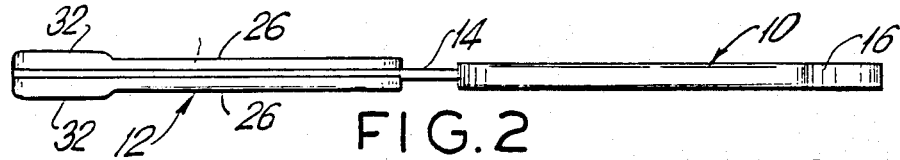
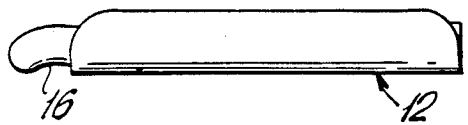
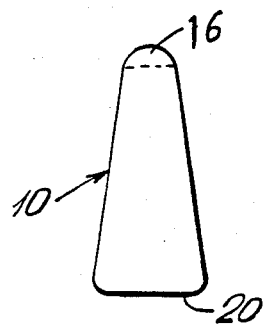
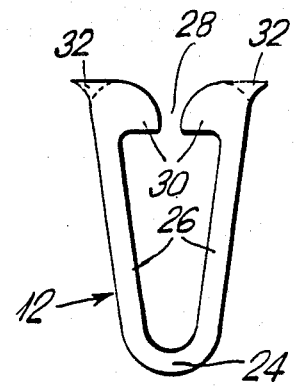
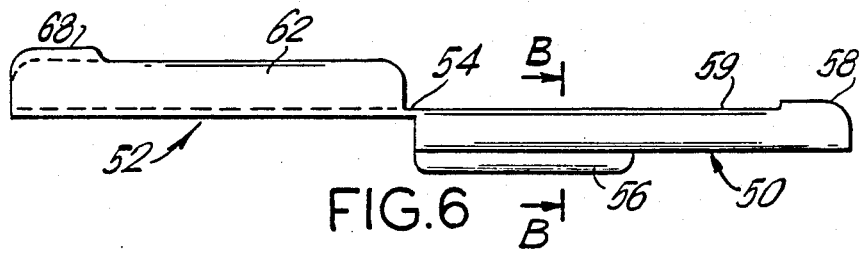
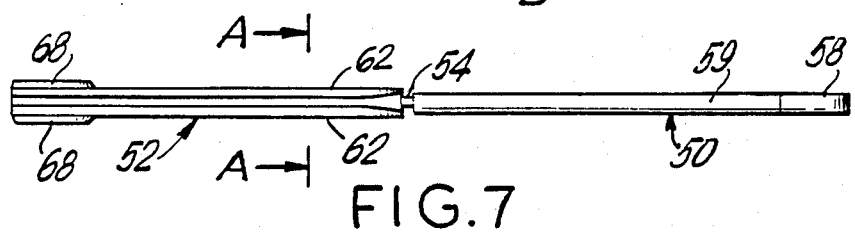
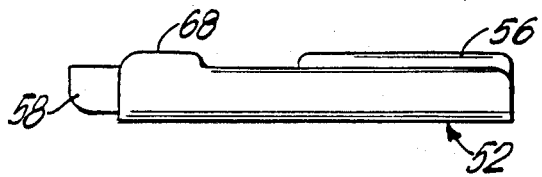

CLIP FOR DRAINABLE OSTOMY POUCH

This is a continuation of copending application Ser. No. 898,871 filed on Aug. 20, 1986 now abandoned which is a continuation of Ser. No. 268,037 filed May 28, 1981, now abandoned.

BACKGROUND OF THE INVENTION

Major abdominal surgery for a number of diseases involving different parts of the gastrointestinal and urinary tract can result in the patient being left with an abdominal stoma. As a result of such surgical procedures, in many cases the ostomate is unable to control the passage of bodily waste material and must rely upon an appliance attached to their body to collect this material. The type of appliance employed varies according to the surgical procedure and the location of the stoma which determines the type and physical consistency of the waste material discharged through the stoma.

Ileostomates and colostomates whose discharge is of a liquid consistency employ systems in which the waste collecting pouch has a bottom opening that permits the contents to be emptied while the pouch remains in place on the body. These pouches include some type of a closure means that seals the drainable bottom opening while the pouch is collecting discharge from the stoma.

Several types of closure means have been developed. For example, Nolan in U.S. Pat. No. 3,523,534 discloses an open ended pouch having a closure consisting of an arcuate blade-like wedge member and a U-shaped trough member. Riely in U.S. Pat. No. 3,690,320 and Burding in U.S. Pat. No. 3,507,282 disclose the use of micro hook and loop elements on the opposite sides of the bottom of the bag that are folded over to seal the bottom of the bag. Fenton in U.S. Pat. No. 3,825,005 discloses an open ended pouch having interlocking ribs and panels on opposite sides of the pouch. Elmore et al in U.S. Pat. No. 3,865,109 and Brown in U.S. Pat. No. 3,618,606 disclose the use of a clamp to seal the open end of the pouch. Fenton in U.S. Pat. No. 2,818,069 disclose the use of a snap type closure. Perry in U.S. Pat. No. 2,638,898 disclose the use of a rubber tube that seals the bottom of the pouch against a metal channel.

SUMMARY OF THE INVENTION

This invention is directed to a clip particularly adapted for use in sealing the open drainage bottom of an ostomy pouch. The clip is of an integral hinged two-limb construction. One limb is held by two opposed resilient catch portions of the other limb within a channel defined by said other limb. The catch portions effect such holding in their normal undeformed positions.

According to a preferred version of the invention there is provided a clip made wholly of synthetic plastics material having two elongated limbs joined by an integral hinge. One limb has a bottom surface and a top surface and increases in width towards the top surface. The other limb is of channel form and open at the top when seen in transverse cross-section and has an opposed pair of overhanging catch portions in the region of its outer end. The hinge is attached to each limb at or near the bottom surface thereof, and the relative dimensions are such that when closed, the said one limb is received in the channel of the other limb and is retained therein by the catch portions.

According to a specially preferred version of the invention, on the limb which has the opposed pair of overhanging catch portions (the second limb), portions of the limb are extended upwardly to provide finger-grippable flanges which stand proud of the upper longitudinal surfaces of said limb.

According to a particular embodiment of the invention, on the first limb an upstanding rib is provided, to serve as a visible and grippable flange when the clip is closed.

The clip is preferably made of polypropylene copolymer.

BRIEF DESCRIPTION OF THE DRAWINGS

FIG. 1 is a side elevation of one example of clip according to the invention in an open condition;

FIG. 2 is a top plan view of the clip of FIG. 1;

FIG. 3 shows a side elevation of the clip in a closed condition;

FIG. 4 is an end view of one limb of the clip of FIGS. 1-3;

FIG. 5 is an end view of the other limb of the clip of FIGS. 1-3;

FIG. 6 is a side elevation of a second example of clip according to the invention in an open condition;

FIG. 7 is a top plan view of the clip in FIG. 6;

FIG. 8 shows a side elevation of the clip according to FIGS. 6 and 7 in the closed condition;

DETAILED DESCRIPTION OF THE INVENTION

Figure 9:
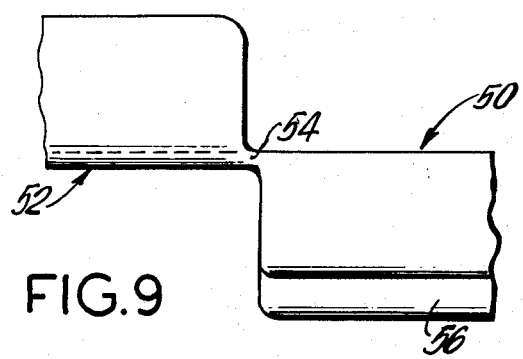
FIG. 9 is a side elevation on an enlarged scale showing a detail of the integral hinge.

The clip illustrated in FIGS. 1-5 is made as a single molding, for example, of a polypropylene copolymer and has one limb 10 and another limb 12 joined by an integral hinge 14. The limb 10 is slightly the longer of the two and has a shaped surface 16 to receive a finger. The hinge may be an integral strip of plastic, for example, of about 0.02 inches square in cross-section.

The limb 10 is of rounded triangular cross-section as best seen in FIG. 4 and increases in width towards its surface 20, which is its top surface when the clip is closed in the orientation shown in FIG. 3. The limb is of substantially constant width along its length at any given height. The other limb is generally of channel form having a base 24, upstanding walls 26, and an open slot 28 at the top (see FIG. 5). Near to one end of the limb 12 (the end opposite to the hinge 14) the top parts of the walls 26 are shaped to provide overhanging catch portions 30 and upwardly and outwardly extending ear portions 32. The latter are provided to assist the user to grip the limb to separate the catch portions, when it is desired to open the clip.

In the normal undeformed position of the walls 26 the catch positions 30 overlie the channel and hold the limb 10 therein. To release the clip, the ears 32 are pushed or pulled laterally outwardly and the limb 10 lifted out of the channel by placing a finger on the surface 16 and lifting. It is found that, in contrast with many prior known clips, the clip can readily be opened with one hand even by an aged and infirm, or non-dexterous user. This is an important feature in a clip whose manipulation is necessary in the unpleasant task of emptying a drainage bag containing bodily waste matter.

An alternative version of clip, intended for the same purpose, is illustrated in FIGS. 6–12. This is basically the same design as the clip illustrated in FIGS. 1–5 but is improved in particular respects to facilitate manipulation.

The clip illustrated in FIGS. 6–12 has a first limb 50 joined to a second limb 52 by an integral hinge 54. The first limb 50 is elongated and bar-like of relatively rigid construction. It is of rounded triangular form and has a rib 56 extending therefrom for part of its length in a direction which is upwardly as seen in FIG. 8 (clip in closed position) and downwardly in FIGS. 6 and 12 (clip in open position). This rib 56 serves as a visible and grippable flange when the clip is in its closed condition as seen in FIG. 8, and stiffens the clip against flexing when the clip is closed.

The limb 50 has, at its end further from the integral hinge 54, a shaped finger portion 58 which, in the closed condition of the clip, extends beyond the confines of the channel-shaped second limb 52. The second limb 52 is generally of channel form having two walls 62, and is V-shaped with a rounded bottom, the radius thereof being slightly greater than the radius of the confronting base portion 59 of the first limb. For example, the radius 63, FIG. 10, may be 0.032 inches and the radius 59, FIG. 12, may be 0.026 inches.

The limb 52 has towards its outer end a pair of overhanging catch portions 64 and these have rounded upper surfaces to allow the limb 50 to be forced therebetween. During this process the sidewalls 62 of the limb 52 are sprung apart due to the inherent resiliency of the material.

Figure 10:
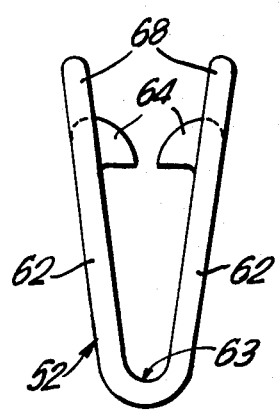
FIG. 10 is an end view of the channel-shaped limb of the clip of FIGS. 6-9.
Figure 11:
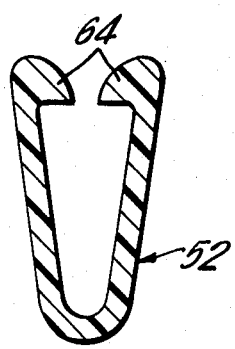
FIG. 11 is a transverse cross-section of the channel-shaped limb shown in FIG. 10 taken on the line A—A in FIG. 7.
Figure 12:
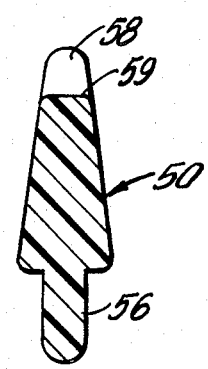
FIG. 12 is a cross-section of the other limb of the clip, taken on the line B—B of FIG. 6.

Finger grippable flanges 68 are provided on the limb 52 over a part of its length, as seen in FIGS. 8 and 10. These flanges provide grippable surfaces which a user can force apart in order to readily unfasten the clip. As shown, the flanges 68 extend about one quarter of the length of the second limb 52, but naturally any suitable dimension may be chosen.

Figure 13:
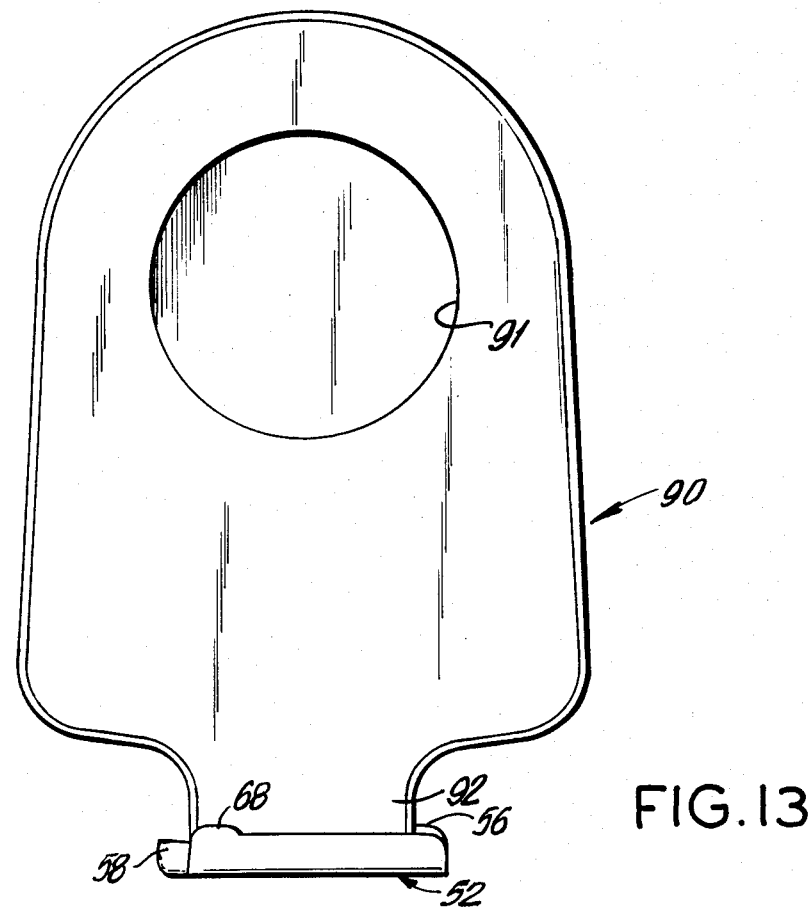
FIG. 13 is a side elevation of the clip of FIGS. 6 to 12 in the closed position sealing the drainable bottom opening of an ostomy pouch.

In use, as shown in FIG. 13, the outlet or tail portion of a drainable ostomy pouch is clamped between the limbs of the clip and when the limbs are closed together is subjected to a reversal of direction of 180 degrees and so is effectively closed off.

The drainage pouch 90 is of conventional construction. It is formed from two polymeric film surfaces permanently sealed along a majority of their edges by heat or other means known in the art. The pouch includes an opening 91 in one of the film surfaces through which the stoma protrudes. The pouch has a generally narrow tail portion 92 whose bottom edge is not sealed and through which the contents of the pouch can be drained.

The pouch 90 can include an adhesive faceplate (not shown in the drawings) around the stomal opening 11 for attachment of the pouch to the body of the ostomate. Alternatively, the pouch 90 can include a mounting element around the stoma opening 91 which fits or locks with a second mounting element adhesively attached to the body of the ostomate. Such a system is described by Steer et al in British Patent No. 1,571,657.

When it is desired to empty the drainage pouch, the user by finger pressure pushes the catch portions apart with the aid of elements 32 or 68 and lifts up on surface 16 or 58.

What is claimed is:

1. A clip of synthetic plastics material having two elongated limbs joined by an integral hinge, a first limb of a rounded triangular cross-section having when the clip is in its closed position a bottom surface and a top surface wherein said first limb increases in width continuously from said bottom surface to said top surface, said first limb being of substantially constant width along its length at any given height, the other limb being of channel form having a base, upstanding walls, and an open slot at the top, said channel limb being V-shaped with a rounded bottom whose radius is slightly greater than the radius of said first limb bottom surface, the top parts of said upstanding walls near the end of said channel limb opposite said hinge are shaped to extend towards each other and provide overhanging catch portions that extend along at least a portion of the length of said channel, said first limb being longer than said limb of channel form, said hinge being attached to each limb at or near the bottom surface thereof, and the relative dimensions being such that when closed the majority of the length of said first limb is received in the channel of said other limb and retained therein by said catch portions with a portion of said first limb extending beyond said channel at the end opposite said hinge.

2. The clip of claim 1 in which said limb of channel form has portions extended to provide finger-grippable flanges which stand proud of the respective upper longitudinal surfaces of said limb.

3. The clip of claim 2 in which said first limb has a rib extending therefrom which in the closed condition of the clip stands proud of the limb of channel form.

4. In combination with a drainable ostomy pouch having an open-bottomed tail portion and means for attaching said pouch to the body around the stoma, a clip of synthetic plastics material for resealably securing said open bottom, said clip having two elongated limbs joined by an integral hinge, a first limb of a rounded triangular cross-section having when the clip is in its closed position a bottom surface and a top surface wherein said first limb increases in width continuously from said bottom surface to said top surface, said first limb being of substantially constant width along its length at any given height, the other limb being of channel form having a base, upstanding walls, and an open slot at the top, said channel limb being V-shaped with a rounded bottom whose radius is slightly greater than the radius of said first limb bottom surface, the top parts of said upstanding walls near the end of said channel limb opposite said hinge are shaped to extend towards each other and provide overhanging catch portions that extend along at least a portion of the length of said channel, said first limb being longer than said limb of channel form, said hinge being attached to each limb at or near the bottom surface thereof, the relative dimensions being such that when closed the majority of the length of said first limb is received in the channel of said other limb and retained therein by said catch portions with a portion of said first limb extending beyond said channel at the end opposite said hinge and wherein the tail portion of said pouch is clamped between said limbs effectively sealing said open-bottom.

5. The combination of claim 4 in which said limb of channel form has portions extended to provide finger-grippable flanges which stand proud of the respective upper longitudinal surfaces of said limb.

6. The combination of claim 5 in which said first limb has a rib extending therefrom which in the closed condition of the clip stands proud of the limb of channel form.

* * * * *